United States Patent [19]

Schmolka

[11] Patent Number: 4,465,663
[45] Date of Patent: Aug. 14, 1984

[54] POLYOXYBUTYLENE-POLYOXYETHYLENE AQUEOUS GELS

[75] Inventor: Irving R. Schmolka, Grosse Ile, Mich.

[73] Assignee: BASF Wyandotte Corporation, Wyandotte, Mich.

[21] Appl. No.: 287,203

[22] Filed: Jul. 27, 1981

[51] Int. Cl.$^3$ .................. A61K 7/06; A61K 7/135
[52] U.S. Cl. .................. 424/62; 424/DIG. 10; 424/65; 424/70; 424/78; 424/278; 424/338; 424/341; 424/358; 424/365; 568/624
[58] Field of Search ............... 424/65, DIG. 10, 338, 424/78, 341, 318, 62, 278; 568/624

[56] References Cited

U.S. PATENT DOCUMENTS

| | | | |
|---|---|---|---|
| 2,828,345 | 3/1958 | Spriggs | 568/624 X |
| 3,057,890 | 10/1962 | De Groote | 568/624 X |
| 3,391,196 | 7/1968 | Earing et al. | 568/624 |
| 3,639,574 | 2/1972 | Schmolka | 424/78 |
| 3,639,575 | 2/1972 | Schmolka | 424/78 |
| 3,740,421 | 6/1973 | Schmolka | 424/78 |
| 3,748,276 | 7/1973 | Schmolka | 568/624 X |
| 3,925,241 | 12/1975 | Schmolka | 424/78 |
| 4,025,525 | 8/1977 | Ackermann | 568/624 X |

*Primary Examiner*—Dale R. Ore
*Attorney, Agent, or Firm*—Bernhard R. Swick

[57] ABSTRACT

Clear aqueous gels prepared from certain polyoxybutylene-polyoxyethylene block polymers are used for topically applied cosmetic and pharmaceutical compositions and remain gels at refrigerator and freezer temperatures.

8 Claims, No Drawings

POLYOXYBUTYLENE-POLYOXYETHYLENE AQUEOUS GELS

BACKGROUND OF THE INVENTION

1. Field of the Invention

Clear, aqueous gels are prepared from certain polyoxybutylene-polyoxyethylene block copolymers. These gels are particularly useful in the formulation of topically applied cosmetic and pharmaceutical compositions because they are gels at temperatures below about 30° C.

2. Description of the Prior Art

U.S. Pat. No. 3,740,421 relates to polyoxyethylene-polyoxypropylene aqueous gels. Polyoxyethylene-polyoxypropylene block copolymers form gels within certain specified ranges of compositions with water. U.S. Pat. No. 3,639,574 relates to hydrogen peroxide gels prepared employing certain polyoxyethylene polyoxypropylene block copolymers as gelling agents. U.S. Pat. No. 3,579,465 relates to polyoxyethylene-polyoxypropylene adducts of ethylene diamine which, within specified limits form aqueous gels. These gels are prepared by dissolving the block copolymer in water at a temperature between 1° C. and 10° C. and thereafter warming to about 30° C. to form the gel.

Among the problems of these prior art gel compositions is that they liquify at temperatures below about 30° C. The gels of U.S. Pat. Nos. 3,740,421, 3,639,575 and 3,579,465 are made at a temperature below at least 10° C., preferably between 1° C. and 7° C. Therefore, they are not gels below about 30° C. and cannot be stored as gels in a refrigerator or freezer. Also, the minimum quantity of the prior art block copolymers needed to make a gel is about 20 percent by weight based on the total gel weight.

It has now been found that block copolymers of polyoxybutylene-polyoxyethylene in aqueous solutions form strong ringing gels which surprisingly do not liquify below about 30° C. Also, the minimum concentration of polyoxybutylene-polyoxyethylene in certain of the block copolymer gels is less than in the above-mentioned prior art gels.

SUMMARY OF THE INVENTION

The invention relates to an aqueous gel comprising from about 84 percent by weight to about 16 percent by weight of water and from about 16 percent by weight to about 84 percent by weight of a polyoxybutylene-polyoxyethylene block copolymer, all weights based on the total weight of the water and the block copolymer aqueous gel. The block copolymer is a cogeneric mixture of conjugated polyoxybutylene-polyoxyethylene compounds containing in their structure oxybutylene groups, oxyethylene groups and an organic radical derived from an organic compound containing a plurality of reactive hydrogen atoms. This is preferably a water-soluble organic compound containing a plurality of reactive hydrogen atoms and 2 to 12 carbon atoms. The compounds are characterized in that all the oxybutylene groups are present in polyoxybutylene chains that are attached to the organic radical at the site of a reactive hydrogen atom thereby principally constituting a polyoxybutylene polymer. The oxyethylene groups are attached to the polyoxybutylene polymer in polyoxyethylene chains. The average molecular weight of the polyoxybutylene polymers in the mixture in at least 1200, as determined by hydroxyl number, and the oxyethylene groups present constitute 45 to 85 percent by weight of the compound with the provisos that (a) when the hydrophobe molecular weight is about 1200, then the minimum polyoxyethylene content is about 60 percent by weight of the block copolymer and the minimum block copolymer content to form a gel is about 25 percent by weight of the gel compositions.

(b) when the hydrophobe molecular weight is about 1800, then the minimum polyoxyethylene content is about 55 percent by weight of the block copolymer and the minimum block copolymer content to form a gel is about 20 percent by weight of the gel composition;

(c) when the hydrophobe molecular weight is about 2400, then the minimum polyoxyethylene content is about 50 percent by weight of the block copolymer and the minimum block copolymer content to form a gel is about 16 percent by weight of the gel composition;

(d) when the hydrophobe molecular weight is about 3000, then the minimum polyoxyethylene content is about 45 percent by weight of the block copolymer and the minimum block copolymer content to form a gel is about 16 percent by weight of the gel composition.

DESCRIPTION OF THE PREFERRED EMBODIMENTS

The polyoxybutylene-polyoxyethylene block copolymer of use in the invention is a cogeneric mixture of conjugated polyoxybutylene-polyoxyethylene compounds having as a hydrophobe, a polyoxybutylene polymer of at least 1200 molecular weight. The polyoxybutylene compounds are prepared by first condensing butylene oxide with an organic compound containing a plurality of reactive hydrogen atoms to prepare a polyoxybutylene polymer of at least 1200 molecular weight, and subsequently condensing ethylene oxide thereto. The compounds used in this invention conform to the following generic formula:

$$Y[(C_4H_8O)_n\text{-}E\text{-}H]_x \qquad (A)$$

wherein Y is the residue of a water soluble organic compound containing therein x active hydrogen atoms; n is an integer; x is an integer greater than 1; the values of n and x are such that the molecular weight of the compound, exclusive of E, is at least 1200, as determined by hydroxyl number; E is a polyoxyalkylene chain wherein the oxygen/carbon atom ratio is at least 0.5, and E constitutes 45 percent by weight to 85 percent by weight of the compound.

The polyoxybutylene polymer, which is an intermediate in the preparation of the compounds of use in this invention, has the following structure:

$$Y[(C_4H_8O)_nH]_x$$

wherein Y, n and x are defined as in Formula A above.

The preferred compounds of use in this invention are prepared by condensing ethylene oxide in an amount between 45 and 85 percent by weight of the resultant compound, with the polyoxybutylene polymer. These compounds have the following formula $$Y[(C_4H_8O)_n(C_2H_4O)_mH]_x$$

wherein Y, n and x are defined as in Formula A and m has a value such that the oxyethylene groups constitute 45 to 85 percent by weight of the compound.

When ethylene oxide is condensed with a polyoxybutylene glycol of at least 1200 molecular weight and derived from a butanediol initiator, the resulting compounds have the following structure:

$$HO(C_2H_4O)_{m'}(C_4H_8O)_n(C_2H_4O)_{m}H$$

where n is defined as previously set forth; and $m' + m$ have a value such that the oxyethylene groups constitute 45 percent by weight to 85 percent by weight of the compound.

The hydrophilic portion of the polyoxyalkylene compounds may be supplied in whole or in part by other polyoxyalkylene chains in lieu of the polyoxyethylene chain set forth in Formula C. Any polyoxyalkylene chain may be used provided that the oxygen/carbon ratio contained therein is at least 0.5.

Examples of a water-soluble organic compound containing therein x active hydrogen atoms, the residue of which is Y, are the initiators which may include water; diols such as propane diol, butanediol, triols such as glycerol, tetrols such as pentaerythritol as well as initiators containing more than four hydroxyl groups such as hexitol or sucrose. Also, amines and other low molecular weight water-soluble compounds having two or more active hydrogen atoms such as ethylene diamine or diethylene triamine may be used as the initiator. Preferably used is butanediol. More preferably used is 1,4-butanediol.

The butylene oxide used in making the hydrophobic polyoxybutylene polymer, which is an intermediate in the preparation of the compounds used in this invention, may be replaced with up to 10 percent by weight of propylene oxide or ethylene oxide when added as a mixture with the butylene oxide. Also, up to 10 percent by weight of propylene oxide or butylene oxide may be used to replace ethylene oxide, when added as a mixture with ethylene oxide, in preparing the block copolymers used in this invention. In lieu of butylene oxide, other 4-carbon cyclic ethers such as methyloxethane, tetrahydrofuran and isobutylene oxide may be used.

As used herein, the term "gel" is defined as a solid or semisolid colloid containing considerable quanitities of water. The particles in a gel are linked in a coherent meshwork which immobilizes the water. The colloidal solution with water as a dispersion medium is often called a "hydrosol". The gels within the scope of the present invention are more specifically "ringing" gels and may be described as gels that have a firm, jelly-like consistency; that is, by tapping the gel lightly, it will vibrate and return to its original configuration.

Illustrative block copolymers of formula D above which may be employed in the preparation of the gels of the present invention, including the molecular weight of the polyoxybutylene hydrophobe, the weight percent of the polyoxyethylene hydrophile as well as the theoretical and found total molecular weights of the copolymer, are presented in Table I. These block copolymers are made from a polyoxybutylene hydrophobe prepared from condensing 1,2-butylene oxide with 1,4-butanediol.

TABLE I

| Block Copolymer | Molecular Weight of Hydrophobe (Avg.) | Weight Percent of Hydrophile (Avg.) | Approximate Total Molecular Weight of Copolymer | |
|---|---|---|---|---|
| | | | T | F |
| A | 1800 | 60 | 4500 | 4200 |
| B | 1800 | 70 | 6000 | 5700 |
| C | 1800 | 80 | 9000 | 8130 |
| D | 1200 | 70 | 4000 | 3765 |
| E | 1200 | 80 | 6000 | 5160 |
| F | 2400 | 60 | 6000 | 5670 |
| G | 2400 | 70 | 8000 | 7800 |
| H | 2400 | 80 | 12,000 | 11,000 |
| I | 3000 | 60 | 7500 | 6165 |
| J | 3000 | 70 | 10,000 | 9000 |
| K | 3000 | 80 | 15,000 | 11,000 |
| L | 1200 | 60 | 3,000 | 2,922 |

Not all of the block copolymers of formula D above may be employed in the present invention. Because of the nature of aqueous solutions of these block copolymers, three variables affect the formation of the gels. These variables are: the weight percent concentration of block copolymers in the aqueous gel, the molecular weight of the hydrophobe $(C_4H_8O)_n$ and the percent by weight of the hydrophile portion $(C_2H_4O)_m + (C_2H_4O)_{m'}$ of the copolymer. These minima define a minimum weight percent concentration of the block copolymer with a specific molecular weight polyoxybutylene hydrophobe having a minimum weight percent of ethylene oxide condensed thereto that is necessary to form a gel. Thus, at the minimum concentration with a specific molecular weight hydrophobe, a minimum weight percent of ethylene oxide is required before a specific block copolymer will form a gel in an aqueous solution. The minimum weight percent concentrations with specific molecular weight hydrophobes are set out in Table II.

Compositions containing water-insoluble organic ingredients, such as N,N-diethyl-m-toluamide and others disclosed in U.S. Pat. No. 3,867,533, lower the minimum weight percent concentration of the block copolymer in the final composition. Therefore, as shown by Examples 12 and 13, a final composition can include a weight percent concentration less than the minimum as disclosed in Table II.

The block copolymer K forms a gel at a minimum concentration of about 16 percent by weight. This is a surprisingly less amount of concentration than the prior art gels, such as a polyoxyethylene polyoxypropylene block copolymer having a hydrophobe molecular weight of about 4000 and containing about 70 percent by weight ethylene oxide, which forms a gel at a minimum of about 20 percent by weight.

TABLE II

| Molecular Weight of Hydrophobe | Minimum Percent by Weight of Block Copolymer to form Gel | Minimum Percent by Weight of Ethylene Oxide Required |
|---|---|---|
| 1200 | 25 | 60 |
| 1800 | 20 | 55 |
| 2400 | 16 | 50 |
| 3000 | 16 | 45 |

The technical explanation for the formation of the gels of the invention is not entirely understood, and the explanation hereinafter is not to be considered as being limitative of the invention. However, the behavior of these block copolymers in forming the gels is believed to be explained on the basis of hydrate formation. It may be speculated that the hydrophobe may, in its own right, immobilize the water independently of the oxyethylene chain by hydrogen bonding. It should be noted that the preferred block copolymers used in the gels of this invention exhibit a hydrophobe lying between two equal hydrophiles. This structure suggests a loose micellar structure is obtained with this class of nonionics and that gel formation would readily involve entrapment of free water in addition to water due to hydrogen bonding.

The gels of the invention may be prepared by (1) dissolving from about 16 to about 84 percent by weight of the polyoxybutylene-polyoxyethylene block copolymer in about 84 to about 16 percent by weight of water at 50° C. and (2) mixing slowly while maintaining the system at 40° C. to 50° C. When a clear solution is obtained, upon cooling to about 30° C., a clear ringing gel is obtained. When ingredients other than water and the polyoxybutylene-polyoxyethylene block copolymers of this invention are used, the other ingredients may be added during step (2) above. Upon cooling, a ringing gel is obtained.

Block copolymers of use in this invention, conforming to structure D above, include those block copolymers which contain a hydrophobe of about 1800 molecular weight and an ethylene oxide content of about 60 percent, used in an amount of at least about 20 percent by weight of the aqueous gel; a hydrophobe of about 1800 molecular weight and an ethylene oxide content of about 65 percent by weight, used in an amount of at least about 20 percent by weight of the aqueous gel; and a hydrophobe of about 1800 molecular weight and an ethylene oxide content of about 70 percent, used in an amount of at least about 20 percent by weight of the aqueous gel; a hydrophobe of about 1200 molecular weight and an ethylene oxide content of about 70 percent by weight, used in an amount of at least about 25 percent by weight; a hydrophobe of about 1200 molecular weight and an ethylene oxide content of about 80 percent by weight, used in an amount of at least about 23 percent by weight; a hydrophobe of about 2400 molecular weight and an ethylene oxide content of about 60 percent by weight, used in an amount of at least about 22 percent by weight; a hydrophobe of about 2400 molecular weight and an ethylene oxide content of about 80 percent by weight, used in an amount of at least about 19 percent by weight; a hydrophobe of about 3000 molecular weight and an ethylene oxide content of about 60 percent by weight, used in an amount of at least about 22 percent by weight. Other gels are formed from block copolymers with hydrophobe molecular weights of 1400, 2000, 2200 and higher. All these gels are distinguished by the fact that they are liquid above about 40° C. to about 60° C., but gel at room or below normal room temperature such as about 25° C. to 30° C.

The aqueous gels of the invention may include various anti-psoriasis drugs, vitamins, and other drugs, any or all of which can be included in these formulations which use a polyoxybutylene-polyoxyethylene gel matrix as a means of supplying the drug to various areas of the body where they are most effective. The aqueous gels of this invention may include a deodorant or an antiperspirant, such as those based on oxyquinoline salts, zinc oxide, etc., an astringent, such as aluminum chlorohydrate; and an antiseptic such as hexachlorodihydroxydiphenylmethane. Also, the gels of this invention may contain hydrogen peroxide; materials for treating planters warts, such as cantharadin, ingredients for treating athletes foot such as undecylenic acid; and insecticides such as N,N-diethyltoluamide.

To those skilled in the cosmetic and pharmaceutical sciences, it will become apparent that these gels may be used in shampoos, in lanolin and oxyethylated lanolin rich skin creams, and with mineral oil for skin and hair products.

The following examples will further illustrate the various aspects of the invention. Where not otherwise specified throughout this specification and claims, temperatures are in degrees centigrade, and parts, percentages and proportions are by weight.

EXAMPLE 1

Block copolymer A, in an amount of 20 parts, was added to 80 parts of distilled water at 50° C. and dissolved by mixing slowly while maintaining the system at 40° C. to 50° C. When a clear solution was obtained, upon cooling, the solution remained liquid until 28° C. and at 20° C. a clear ringing gel was obtained.

EXAMPLES 2-9

Gels were prepared using the general procedure of Example 1. The block copolymer used, percent by weight of block copolymer in solution, and gel/liquid temperatures are shown below in Table III. The gel/liquid temperatures reflect the temperatures below which the system is a gel and above which the system is a liquid.

TABLE III

| Block Copolymer | Percent by Weight of Block Copolymer in Gel | Gel/Liquid Temperature °C. |
| --- | --- | --- |
| B | 20 | 46/50 |
| C | 20 | 49/55 |
| D | 25 | 47/50 |
| E | 23 | 49/52 |
| F | 22 | 34/38 |
| H | 19 | 44/50 |
| I | 22 | 25/29 |
| L | 25 | 24/29 |
| L | 26 | 37/42 |

Examples 10-14 show practical applications of the ringing gels. The procedure used is as follows: The block copolymer was dissolved in the water as generally described in Example 1. The other ingredients were added to the solution while maintaining the temperature of the system between 40° and 50° C. Upon obtaining a solution, and cooling to about 30° C., a ringing gel is obtained.

EXAMPLE 10

A gel is prepared with hydrogen peroxide for use in bleaching hair or treating poison ivy or poison oak, from the following formulation:

| Component | Parts by Weight |
| --- | --- |
| 30% Hydrogen peroxide | 10 |
| Block Copolymer A | 22 |
| Water | 68 |

EXAMPLE 11

A gel composition is prepared for treating planter's warts. A cantharidin is suspended in Block Copolymer A gel matrix of the following formulation:

| Component | Parts by Weight |
| --- | --- |
| Cantharidin | 10 |
| Propylene glycol | 3 |
| Block Copolymer A | 22 |
| Water | 64 |

EXAMPLE 12

An insect repellant gel is formed from the following formulation:

| Component | Parts by Weight |
| --- | --- |
| Block Copolymer A | 18 |
| Isopropyl Alcohol | 12 |
| N,N—diethyltoluamide | 10 |
| Water | 60 |
| Preservative | q.s. |

EXAMPLE 13

An athlete's foot gel is prepared from the following formulation:

| Component | Parts by Weight |
| --- | --- |
| Block Copolymer A | 18 |
| Undecylenic Acid | 5 |
| Isopropyl Alcohol | 17 |
| Water | 60 |

All of the above formulations remained gels at temperatures below about 30° C.

EXAMPLE 14

An athlete's foot gel is prepared from the following formulation:

| Component | Parts by Weight |
| --- | --- |
| Block Copolymer H | 20 |
| Undecylenic Acid | 5 |
| Isopropyl Alcohol | 17 |
| Water | 60 |

The embodiments of the invention in which an exclusive privilege or property is claimed are defined as follows:

1. A gel composition which remains a gel at temperatures below room temperature comprising from about 84 percent by weight to about 16 percent by weight of water and from about 16 percent by weight to about 84 percent by weight of a polyoxybutylene-polyoxyethylene block copolymer, all weights based on the weight of the water and the block copolymer wherein said block copolymer is a cogeneric mixture of conjugated polyoxybutylene-polyoxyethylene compounds containing in their structure oxybutylene groups, oxyethylene groups and an organic radical derived from a water-soluble organic compound containing a plurality of reactive hydrogen atoms and 2 to 12 carbon atoms; the compounds being characterized in that all of the oxybutylene groups are present in polyoxybutylene chains that are attached to the organic radical at the site of a reactive hydrogen atom thereby constituting a polyoxybutylene polymer; the oxyethylene groups being attached to the polyoxybutylene polymer in polyoxyethylene chains; the average molecular weight of the polyoxybutylene polymers in the mixture being at least 1200, as determined by hydroxyl number, and the oxyethylene groups present constituting 45 and 85 percent by weight of the mixture, with the provisos that (a) when the hydrophobe molecular weight is about 1200, then the minimum polyoxyethylene content is about 60 percent by weight of the block copolymer and the minimum block copolymer content to form a gel is about 25 percent by weight of the gel composition;

(b) when the hydrophobe molecular weight is about 1800, then the minimum polyoxethylene content is about 55 percent by weight of the block copolymer and the minimum block copolymer content to form a gel is about 20 percent by weight of the gel composition;

(c) when the hydrophobe molecular weight is about 2400, then the minimum polyoxyethylene content is about 50 percent by weight of the block copolymer and the minimum block copolymer content to form a gel is about 16 percent by weight of the gel composition;

(d) when the hydrophobe molecular weight is about 3000, then the minimum polyoxyethylene content is about 45 percent by weight of the block copolymer and the minimum block copolymer content to form a gel is about 16 percent by weight of the gel composition.

2. The composition of claim 1 wherein the polyoxybutylene polymer has a molecular weight of about 1800.

3. The composition of claim 1 wherein the polyoxybutylene polymer has a molecular weight of about 1800 and a polyoxyethylene content of about 60 percent by weight of the mixture.

4. The composition of claim 1 additionally comprising an effective amount of a member selected from the group consisting of an antipsoriasis drug, a vitamin, an antiperspirant, an antiseptic, mineral oil, lanolin, oxyethylated lanolin, hydrogen peroxide, insecticide, athletes foot treating ingredient and plantar wart treating material.

5. The composition of claim 1 wherein the polyoxybutylene polymer has a molecular weight of about 2400.

6. The composition of claim 1 wherein the polyoxybutylene polymer has a molecular weight of about 2400 and a polyoxyethylene content of about 80 percent by weight of the mixture.

7. The composition of claim 1 wherein the polyoxybutylene polymer has a molecular weight of about 3000.

8. The composition of claim 1 wherein the polyoxybutylene polymer has a molecular weight of about 3000 and a polyoxyethylene content of about 60 percent by weight of the mixture.

* * * * *